(12) United States Patent
Kai et al.

(10) Patent No.: US 8,795,848 B2
(45) Date of Patent: Aug. 5, 2014

(54) INDOLOCARBAZOLE DERIVATIVE WITH FUSED HETEROCYCLIC AROMATIC GROUP FOR ORGANIC ELECTROLUMINESCENT DEVICE AND ORGANIC ELECTROLUMINESCENT DEVICE CONTAINING SAME

(75) Inventors: Takahiro Kai, Kitakyushu (JP); Masaki Komori, Kitakyushu (JP); Toshihiro Yamamoto, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 292 days.

(21) Appl. No.: 12/991,129

(22) PCT Filed: Apr. 30, 2009

(86) PCT No.: PCT/JP2009/058524
§ 371 (c)(1),
(2), (4) Date: Nov. 5, 2010

(87) PCT Pub. No.: WO2009/136595
PCT Pub. Date: Nov. 12, 2009

(65) Prior Publication Data
US 2011/0062429 A1    Mar. 17, 2011

(30) Foreign Application Priority Data
May 8, 2008    (JP) .................... 2008-122059

(51) Int. Cl.
| | |
|---|---|
| H01L 51/54 | (2006.01) |
| C09K 11/06 | (2006.01) |
| C07D 487/04 | (2006.01) |
| C07D 471/04 | (2006.01) |
| C07D 471/14 | (2006.01) |
| C09B 57/00 | (2006.01) |
| C09B 47/00 | (2006.01) |
| C09B 67/22 | (2006.01) |
| C09B 57/10 | (2006.01) |
| H01L 51/00 | (2006.01) |
| H05B 33/20 | (2006.01) |
| H01L 51/50 | (2006.01) |

(52) U.S. Cl.
CPC ......... *C09K 11/06* (2013.01); *C09K 2211/1011* (2013.01); *C09B 57/00* (2013.01); *C09B 47/00* (2013.01); *C09B 67/0033* (2013.01); *H01L 51/5016* (2013.01); *C09K 2211/1029* (2013.01); *C09B 57/10* (2013.01); *C09K 2211/185* (2013.01); *H01L 51/0072* (2013.01); *C07D 487/04* (2013.01); *C09K 2211/1007* (2013.01); *H05B 33/20* (2013.01); *C09K 2211/1044* (2013.01); *Y10S 428/917* (2013.01)
USPC ............ 428/690; 428/917; 257/40; 313/504; 546/88; 546/160; 546/167; 548/418

(58) Field of Classification Search
None
See application file for complete search history.

(56) References Cited

U.S. PATENT DOCUMENTS
| | | | |
|---|---|---|---|
| 5,843,607 A | 12/1998 | Hu et al. | |
| 2002/0034655 A1 | 3/2002 | Watanabe et al. | |

(Continued)

FOREIGN PATENT DOCUMENTS
| | | |
|---|---|---|
| EP | 1 956 022 A1 | 8/2008 |
| JP | 11-167215 A | 6/1999 |

(Continued)

OTHER PUBLICATIONS

English Translation of International Preliminary Report on Patentability and Written Opinion of the International Searching Authority, dated Dec. 23, 2010, for International Application No. PCT/JP2009/058524 (Forms PCT/IB/338, PCT/IB/373 and PCT/ISA/237).

(Continued)

*Primary Examiner* — Andrew K Bohaty
(74) *Attorney, Agent, or Firm* — Birch, Stewart, Kolasch & Birch, LLP

(57) ABSTRACT

Disclosed is an organic electroluminescent device (organic EL device) that is improved in the luminous efficiency, fully secured of the driving stability, and of a simple structure and also disclosed is a compound for organic EL device useful for the said device. The compound for organic EL device is, for example, an indolocarbazole derivative represented by the following general formula (3). The organic EL device comprises a light-emitting layer disposed between an anode and a cathode piled one upon another on a substrate and the said light-emitting layer comprises a phosphorescent dopant and the aforementioned indolocarbazole derivative as a host material. In general formula (3), L is an aromatic heterocyclic group of a fused-ring structure with a valence of (n+1), $Ar_1$ to $Ar_3$ each is an alkyl group, an aralkyl group, or a substituted or unsubstituted aromatic hydrocarbon or aromatic heterocyclic group, and n is an integer of 0-5.

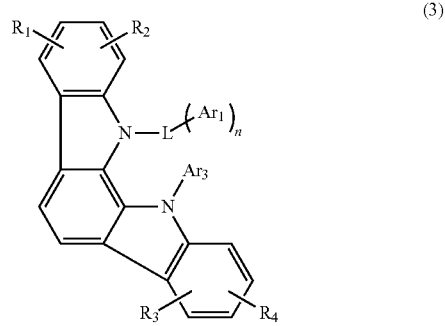

(3)

10 Claims, 1 Drawing Sheet

(56) References Cited

U.S. PATENT DOCUMENTS

| | | | |
|---|---|---|---|
| 2004/0137271 A1 | 7/2004 | Sohn et al. | |
| 2006/0124921 A1 | 6/2006 | Ong et al. | |
| 2008/0220285 A1 | 9/2008 | Vestweber et al. | |
| 2009/0302742 A1* | 12/2009 | Komori et al. | 313/504 |
| 2009/0302743 A1* | 12/2009 | Kato et al. | 313/504 |
| 2010/0148161 A1 | 6/2010 | Kai et al. | |

FOREIGN PATENT DOCUMENTS

| | | |
|---|---|---|
| JP | 2001-313178 A | 11/2001 |
| JP | 2004-204234 A | 7/2004 |
| JP | 2006-193729 A | 7/2006 |
| WO | WO 01/41512 A1 | 6/2001 |
| WO | WO 2006/122630 A1 | 11/2006 |
| WO | WO 2007/063754 A1 | 6/2007 |
| WO | WO 2008/146839 A1 | 12/2008 |

OTHER PUBLICATIONS

International Search Report, dated Jun. 9, 2009, issued in PCT/JP2009/058524.

International Preliminary Report of Patentability for PCT/JP2009/058524 dated Nov. 9, 2010 (Forms PCT/IB/326, PCT/IB/373 and PCT/ISA/237).

* cited by examiner

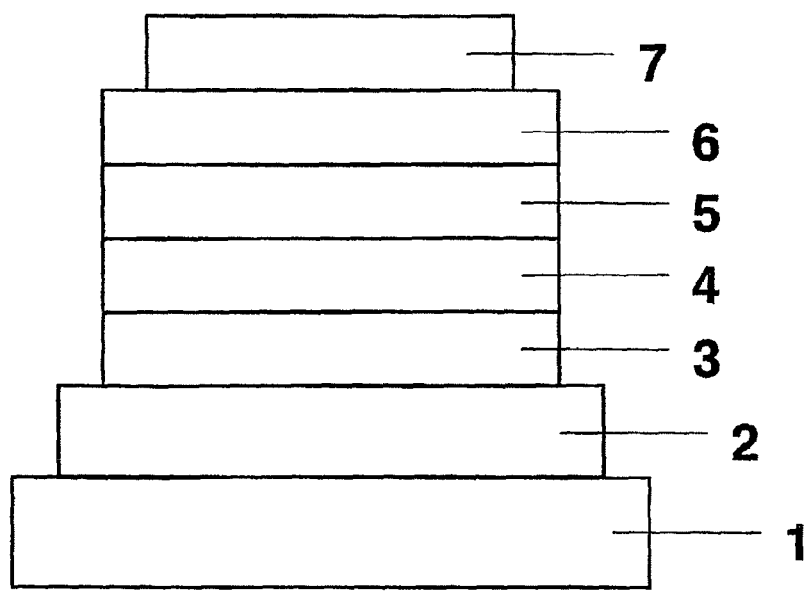

US 8,795,848 B2

INDOLOCARBAZOLE DERIVATIVE WITH FUSED HETEROCYCLIC AROMATIC GROUP FOR ORGANIC ELECTROLUMINESCENT DEVICE AND ORGANIC ELECTROLUMINESCENT DEVICE CONTAINING SAME

FIELD OF TECHNOLOGY

This invention relates to a novel compound for organic electroluminescent device and to an organic electroluminescent device (hereinafter referred to as organic EL device) using the said novel compound.

BACKGROUND TECHNOLOGY

An organic electroluminescent device in the simplest structure is generally constituted of a light-emitting layer and a pair of counter electrodes sandwiching the said light-emitting layer. The device functions by utilizing the following phenomenon; upon application of an electrical field between the electrodes, electrons are injected from the cathode and holes are injected from the anode and they recombine in the light-emitting layer with emission of light.

In recent years, organic thin films have been used in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been directed toward commercial applications to high-performance flat panels featuring self-luminescence and high-speed response.

In another effort to enhance the luminous efficiency of the device, the use of phosphorescence in place of fluorescence is investigated. The aforementioned device comprising a hole-transporting layer composed of an aromatic amine and a light-emitting layer composed of Alq3 and many other devices utilize fluorescence. The use of phosphorescence, that is, emission of light from the excited triplet state, is expected to enhance the luminous efficiency three to four times that of the conventional devices utilizing fluorescence (emission of light from the excited singlet state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they failed to emit light at high efficiency. In recent years, as is mentioned in patent document 1, a large number of researches are conducted with the objective of enhancing the luminous efficiency and extending the lifetime while giving priority to utilization of organic metal complexes such as iridium complexes.

Patent document 1: JP2003-515897 A
Patent document 2: JP2001-313178 A
Patent document 3: JP2002-352957 A
Patent document 4: JP 11-162650 A
Patent document 5: JP 11-176578 A
Patent document 6: WO2007/063796

In order to enhance the luminous efficiency, a host material to be used together with a dopant material becomes important. Of the host materials proposed thus far, a typical example is 4,4'-bis(9-carbazolyl)biphenyl (hereinafter referred to as CBP), a carbazole compound cited in patent document 2. When CBP is used as a host material for tris(2-phenylpyridine)iridium complex (hereinafter referred to as Ir(ppy)3), a phosphorescent material emitting green light, the balance of electrical charges in the light-emitting layer is destroyed and excess holes flow out to the side of the cathode on account of the electron transport property being inferior to the hole transport property in the case of CBP and the result is lowering of the luminous efficiency due to lowering of the recombination probability in the light-emitting layer. Furthermore, in this case, the recombination zone in the light-emitting layer is limited to a narrow space in the vicinity of the interface on the cathode side. Consequently, in the case where an electron-transporting material, such as Alq3, whose lowest triplet energy level is lower than that of Ir(ppy)3 is used, there may arise a possibility that the luminous efficiency becomes lower due to transfer of the triplet energy from the dopant to the electron-transporting material.

On the other hand, 3-phenyl-4-(1'-naphthyl)-5-phenyl-1,2,4-triazole (hereinafter referred to as TAZ), disclosed in patent document 3, is also proposed as a host material for a phosphorescent organic EL device. As the hole transport property is inferior to the electron transport property in the case of TAZ, the light-emitting zone is on the side of the hole-transporting layer. In this case, the chosen hole-transporting material influences the luminous efficiency of Ir(ppy)3. For example, the use of 4,4'-bis[N-(1-naphthyl)-N-phenylamino]biphenyl (hereinafter referred to as NPB), a material in widespread use for its good performance, high reliability, and long life, in the hole-transporting layer causes a problem that transfer of the triplet energy occurs from Ir(ppy)3 to NPB reflecting the relationship of the lowest triplet energy level between the two and the luminous efficiency becomes lower.

Furthermore, compounds like CBP and TAZ readily undergo crystallization and agglomeration with the resultant deterioration of the shape of thin film. In addition, the Tg of such compounds is difficult to merely observe because of their high crystallinity. The instability of the shape of thin film in the light-emitting layer exerts an adverse influence on the device such as shortening of the lifetime and lowering of the heat resistance.

As the aforementioned examples indicate, it can readily be understood that a demand is created for host materials that possess simultaneously a high hole transport property and a high electron transport property and are well balanced in the electrical charges (hole and electron) transport properties. Furthermore, it is desirable that the host materials are endowed with electrochemical stability, high heat resistance, and good stability in the amorphous state.

Further, although patent documents 4, 5, and 6 disclose the use of a certain kind of indolocarbazole compounds in organic EL devices, there is a strong demand for compounds with better properties for use in organic EL devices.

DISCLOSURE OF THE INVENTION

In applications of organic EL devices to display devices such as flat panel displays, it is necessary to enhance the luminous efficiency of the device and, at the same time, to fully secure the driving stability of the device. Under the aforementioned circumstances, an object of this invention is to provide an organic EL device of high efficiency, good driving stability, and practical usefulness and to provide a compound suitable therefor.

The inventors of this invention have conducted intensive studies, found as a result that the use of compounds of a specified structure in organic EL devices solves the aforementioned problems, and completed this invention.

Accordingly, this invention relates to an organic EL device using a compound of a specified indolocarbazole skeleton.

According to this invention, a compound for organic electroluminescent device is represented by the following general formula (1).

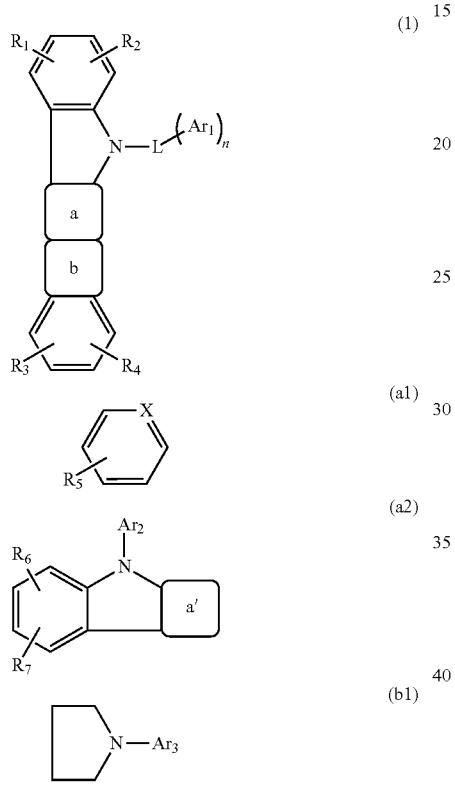

In general formula (1), ring a is an aromatic or heterocyclic ring fused to two adjacent rings and represented by formula (a1) or (a2), ring a' is an aromatic or heterocyclic ring fused to three adjacent rings and represented by formula (a1), and ring b is a heterocyclic ring fused to two adjacent rings and represented by formula (b1); X is CR or N; L is an aromatic heterocyclic group of a fused-ring structure with a valence of (n+1); $Ar_1$ to $Ar_3$ each is independently an alkyl group, an aralkyl group, or a substituted or unsubstituted aromatic hydrocarbon or aromatic heterocyclic group and $Ar_2$ and $Ar_3$ are never nitrogen-containing six-membered rings; R and $R_1$ to $R_7$ each is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, or a substituted or unsubstituted aromatic hydrocarbon or aromatic heterocyclic group and in the case where any two of the foregoing are located adjacent to each other, they may be linked to form a ring; n is an integer of 0-5.

The compounds for organic electroluminescent devices represented by general formula (1) include compounds represented by the following general formula (2) or (3).

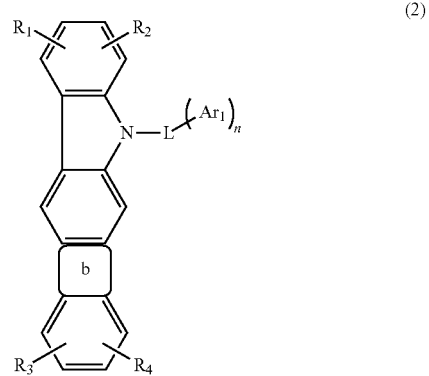

In general formula (2), ring b, L, $Ar_1$, $R_1$ to $R_4$, and n respectively have the same meaning as ring b, L, $Ar_1$, $R_1$ to $R_4$, and n in general formula (1).

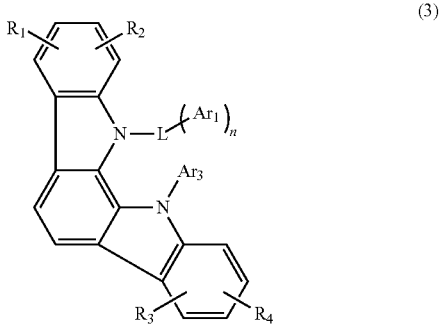

In formula (3), L, $Ar_1$, $Ar_3$, $R_1$ to $R_4$, and n respectively have the same meaning as L, $Ar_1$, $Ar_3$, $R_1$ to $R_4$, and n in general formula (1).

Further, this invention relates to an organic electroluminescent device that comprises an organic layer comprising the aforementioned compound for organic electroluminescent device. Advantageously, the said organic layer is at least one layer selected from a light-emitting layer, a hole-transporting layer, a hole-injecting layer, an electron-transporting layer, an electron-injecting layer, and a hole-blocking layer. More advantageously, this invention relates to an organic electroluminescent device in which the organic layer is a light-emitting layer and the said light-emitting layer comprises a phosphorescent dopant and the aforementioned compound for organic electroluminescent device as a host material.

BRIEF DESCRIPTION OF THE DRAWING

FIG. 1 shows the cross section of an example of an organic EL device.

PREFERRED EMBODIMENTS OF THE INVENTION

The compound for organic EL device of this invention is represented by the aforementioned general formula (1). Any of the compounds represented by general formula (1) typically has an indolocarbazole skeleton formed by fusion of a carbazole ring and an indole ring. The N atom in the carbazole ring is linked to L, an aromatic heterocyclic group of a fused-ring structure.

In general formula (1), ring a is an aromatic or heterocyclic ring fused to two adjacent rings and represented by formula (a1) or (a2). In the case where ring a is a heterocyclic ring represented by formula (a2), ring a' is an aromatic or heterocyclic ring fused to three adjacent rings and represented by formula (a1). In formula (a1), X is CR or N. Here, R is a group similar to $R_1$ to $R_7$ and it is preferably a hydrogen atom. Ring b is a heterocyclic ring fused to two adjacent rings and represented by formula (b1).

In general formula (1), L is an aromatic heterocyclic group of a fused-ring structure with a valence of (n+1). Here, n is an integer of 0-5, preferably an integer of 0-2.

Preferable examples of aromatic heterocyclic groups of a fused-ring structure are the groups formed by removing (n+1) hydrogen atoms from the aromatic heterocyclic compounds shown below.

Concretely, examples of the aforementioned aromatic heterocyclic compounds include benzothiophene, benzothiazole, thianthrene, isobenzofuran, benzoxazole, chromene, xanthene, phenoxathiin, indolizine, isoindole, indole, benzimidazole, indazole, benzotriazole, purine, quinolizine, isoquinoline, quinoline, phthalazine, naphthyridine, quinoxaline, quinazoline, cinnoline, pterizine, carbazole, carboline, phenanthridine, acridine, perimidine, phenanthroline, phenazine, phenothiazine, phenoxazine, and dibenzodioxin.

In general formulas (1), (2), and (3), $Ar_1$ to $Ar_3$ each is independently an alkyl group, an aralkyl group, or a substituted or unsubstituted aromatic hydrocarbon or aromatic heterocyclic group. However, $Ar_2$ and $Ar_3$ are never nitrogen-containing six-membered rings when the two are aromatic heterocyclic groups.

In general formulas (1), (2), and (3), the number of carbon atoms in $Ar_1$ to $Ar_3$ is preferably 1 to 6 in the case of an alkyl group, 7 to 13 in the case of an aralkyl group, or 3 to 15 in the case of a substituted or unsubstituted aromatic hydrocarbon or aromatic heterocyclic group.

Preferable examples of the unsubstituted aromatic hydrocarbon groups are the monovalent groups formed by removing one hydrogen atom from benzene, naphthalene, anthracene, phenanthrene, indene, biphenyl, terphenyl, and quaterphenyl. More preferable are the monovalent groups formed by removing one hydrogen atom from benzene, biphenyl, and terphenyl.

Preferable examples of the unsubstituted aromatic heterocyclic groups include the monovalent groups formed by removing one hydrogen atom from thiophene, thiazole, furan, oxazole, pyran, pyrrole, imidazole, pyrazole, isothiazole, isoxazole, frazan, triazole, pyridine, pyrazine, pyrimidine, pyridazine, triazine, benzothiophene, benzothiazole, thianthrene, isobenzofuran, benzoxazole, chromene, xanthene, phenoxathiin, indolizine, isoindole, indole, benzimidazole, indazole, benzotriazole, purine, quinolizine, isoquinoline, quinoline, phthalazine, naphthyridine, quinoxaline, quinazoline, cinnoline, pterizine, carbazole, carboline, phenanthridine, acridine, perimidine, phenanthroline, phenazine, phenothiazine, phenoxazine, and dibenzodioxin. More preferable are the monovalent groups formed by removing one hydrogen atom from pyridine, pyrazine, pyrimidine, pyridazine, and triazine.

The groups $R_1$ to $R_7$ each is independently hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, or a substituted or unsubstituted aromatic hydrocarbon or aromatic heterocyclic group. In the case where any two of the foregoing are located adjacent to each other, they may be linked to form a fused ring. Preferably, $R_1$ to $R_7$ each is hydrogen or an alkyl group.

In the case where $R_1$ to $R_7$ each is an alkyl group, the number of carbon atoms in such alkyl group is preferably 1 to 6. Likewise, the number of carbon atoms is preferably 2 to 6 in the case of an alkenyl or alkynyl group, 7 to 13 in the case of an aralkyl group, 3 to 15 in the case of a substituted or unsubstituted aromatic hydrocarbon or aromatic heterocyclic group, 2 to 10 in the case of a dialkylamino group, 6 to 20 in the case of a diarylamino or diaralkylamino group, 2 to 10 in the case of an acyl or alkoxycarbonyl group, and 1 to 6 in the case of an alkoxyl, alkylsulfonyl, or haloalkyl group.

In the case where any two of $R_1$ to $R_7$ are located adjacent to each other, they may be linked together to form a fused ring. For example, when two vinyl groups are located adjacent to each other, the carbon atoms in the vinyl groups and two carbon atoms in the indolocarbazole skeleton carrying the vinyl groups are linked together to form a six-membered ring and the result is the formation of a nitrogen-containing compound of six fused rings. In the case where there are two pairs of adjacent substituents, there may be a possibility of the formation of a nitrogen-containing compound of seven fused rings.

In the case where the aforementioned groups $Ar_1$ to $Ar_3$ and $R_1$ to $R_7$ are substituted aromatic hydrocarbon or aromatic heterocyclic groups, preferable substituents include an alkyl group of 1 to 6 carbon atoms, an alkoxyl group of 1 to 6 carbon atoms, an aryloxy group of 6 to 12 carbon atoms, an alkylthio group, a substituted amino group, an acetyl group, a phenyl group, a biphenylyl group, a terphenylyl group, a naphthyl group, a pyridyl group, a pyrimidyl group, a triazyl group, an imidazolyl group, a thienyl group, and a carbazolyl group.

General formulas (2) and (3) show preferred forms of general formula (1); ring a in general formula (1) is specified as a benzene ring in general formula (2) and the mode of linkage of ring b is specified in general formula (3).

The compounds for organic EL device of this invention can be prepared easily by one of known methods. For example, a compound represented by general formula (1) can be prepared by a sequence of reactions illustrated below with reference to a synthetic example described in Synlett., 2005, No. 1, pp. 42-48.

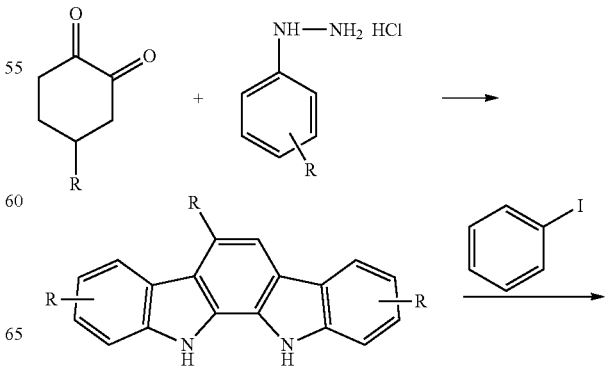

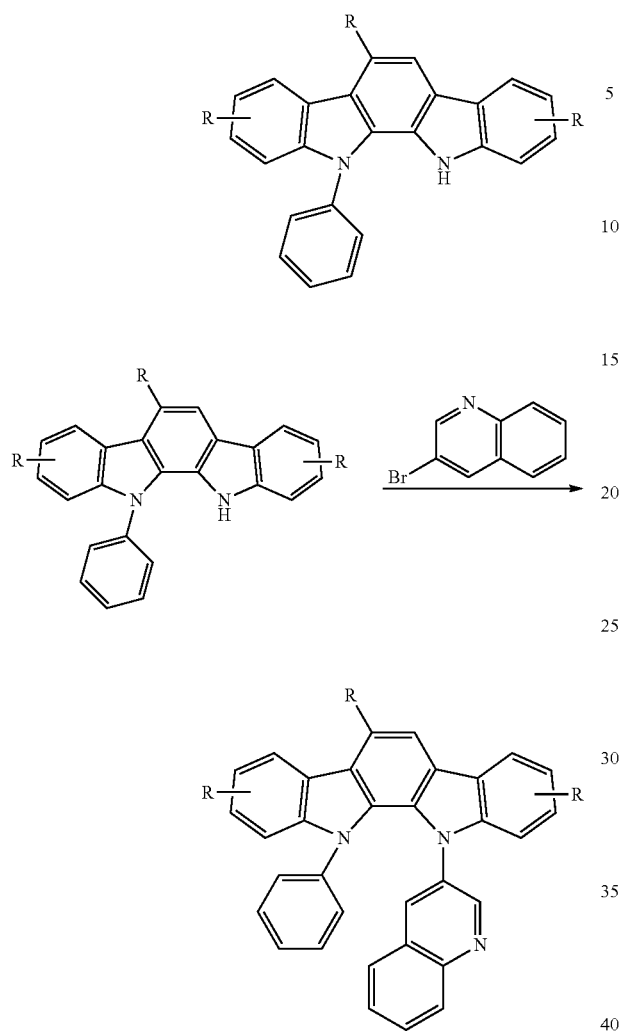
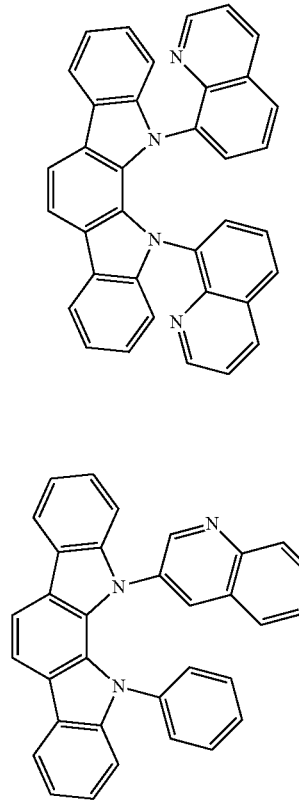
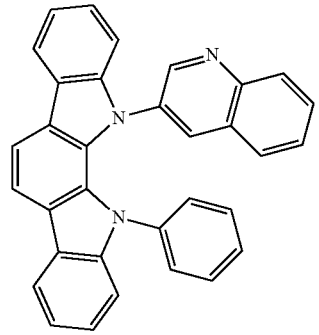
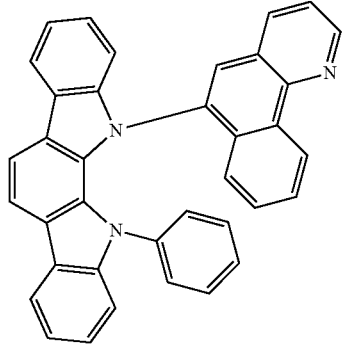
Preferable examples of the compounds represented by general formula (1) or by general formulas (2) and (3) are shown below, but are not limited thereto.
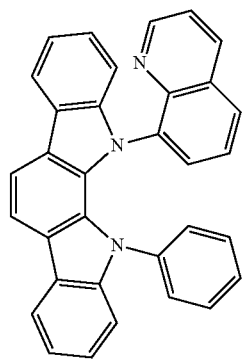
(1)
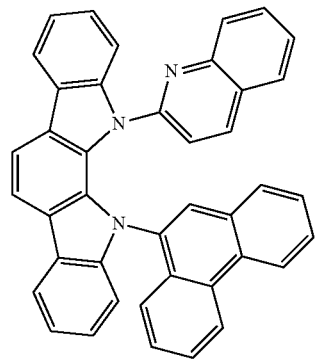
(5)

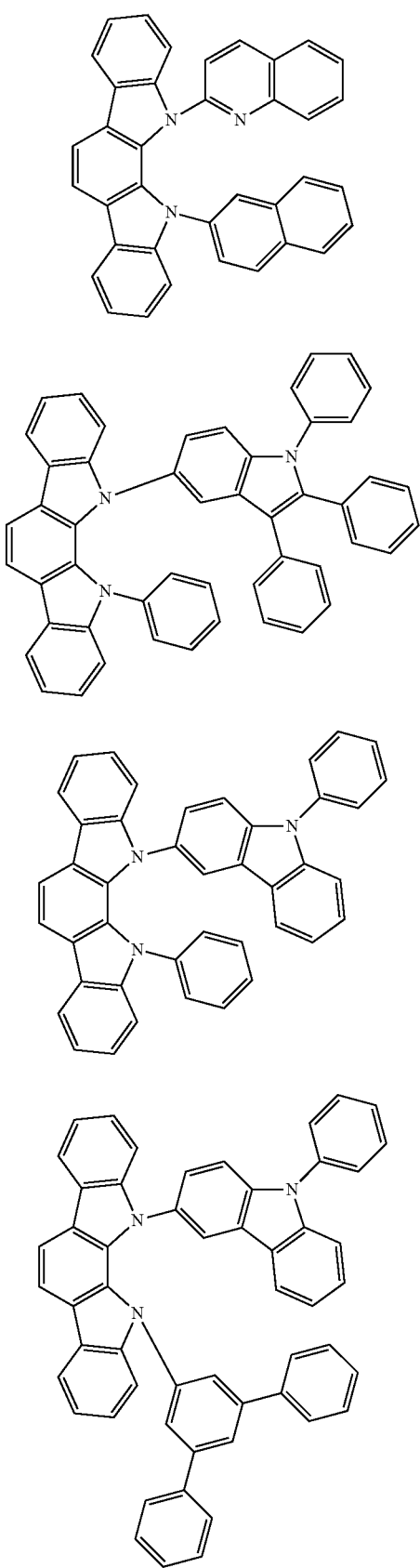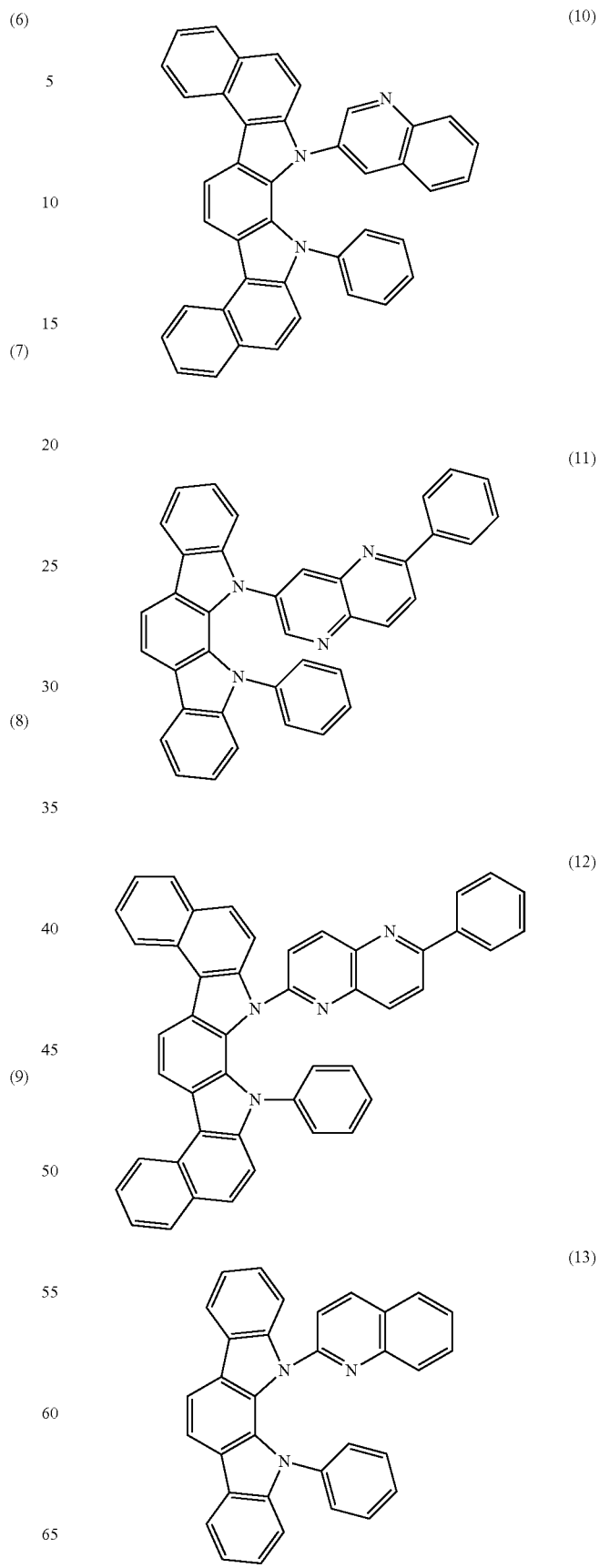

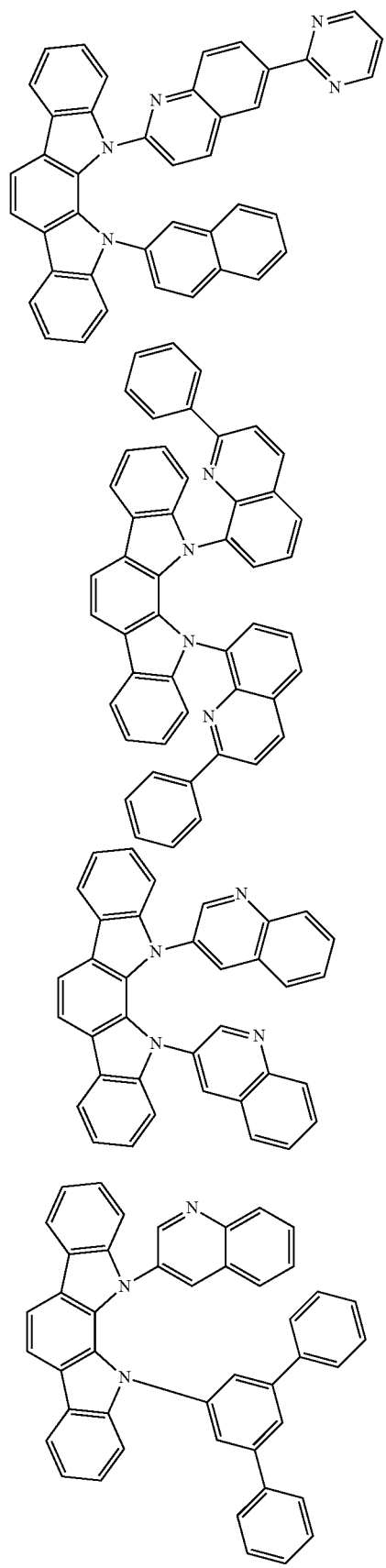
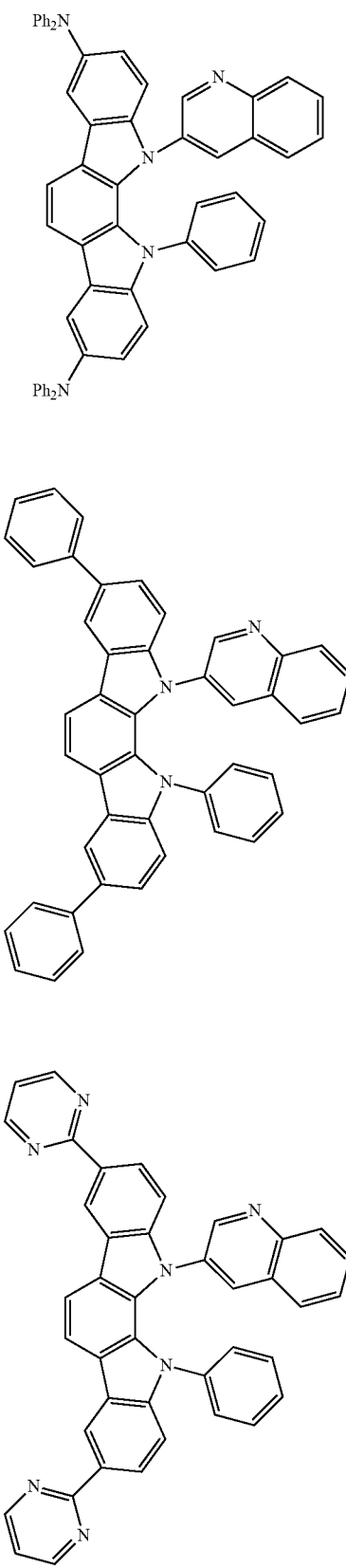

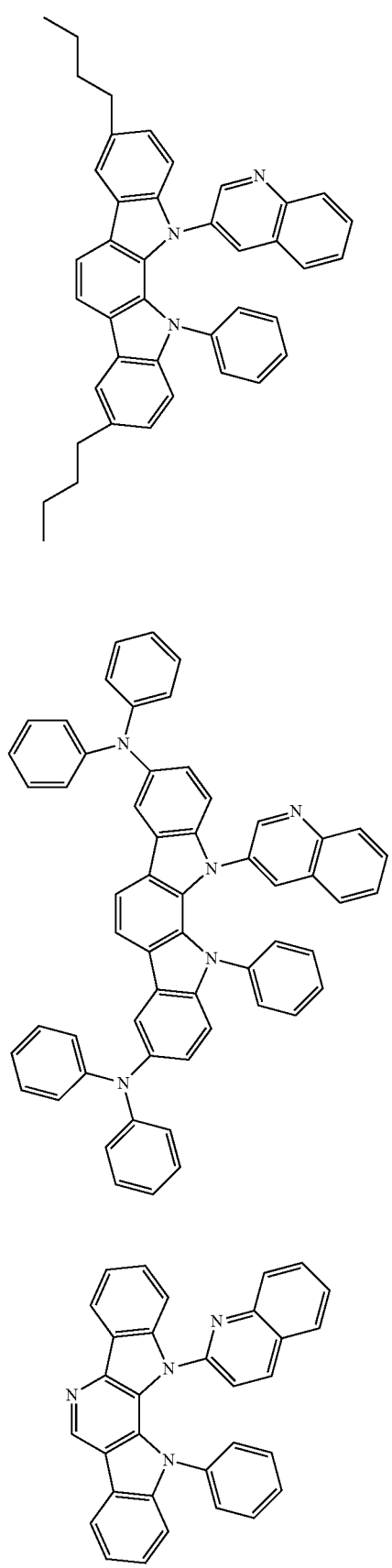
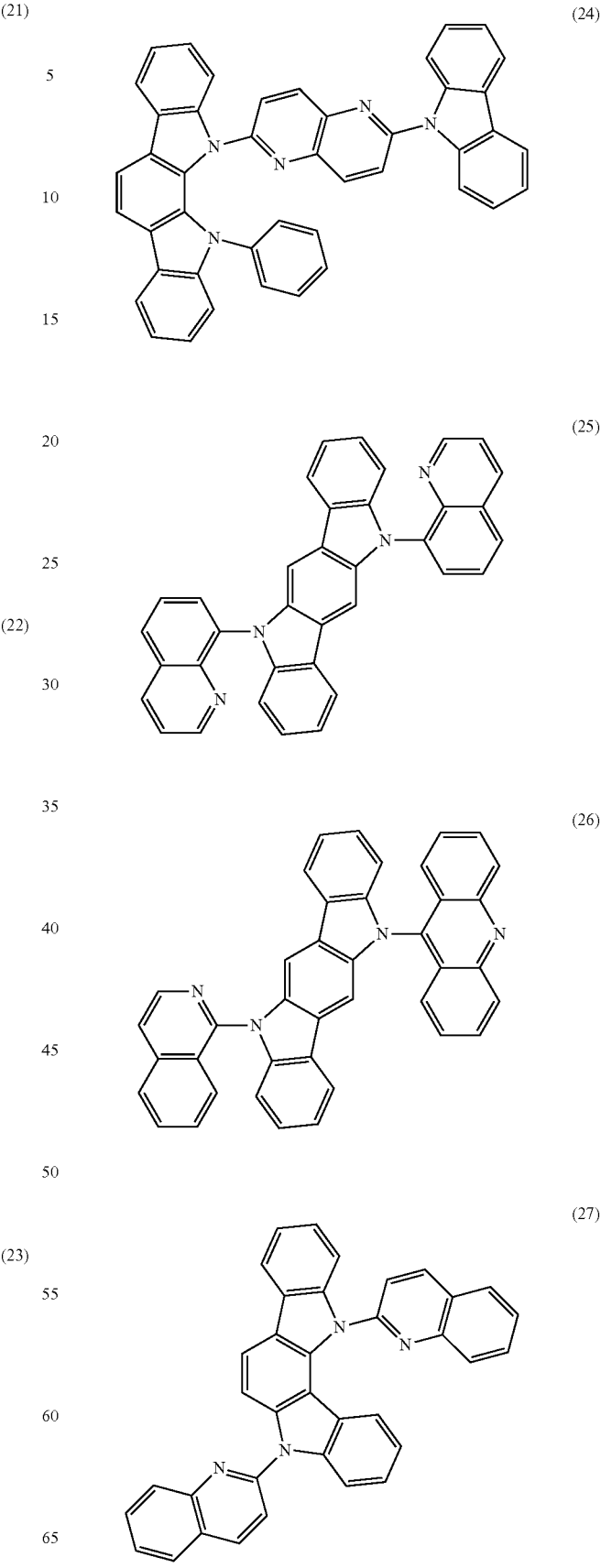

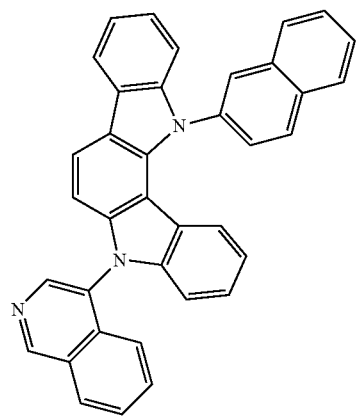
(28)
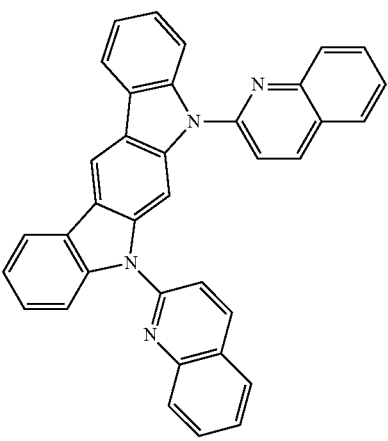
(32)
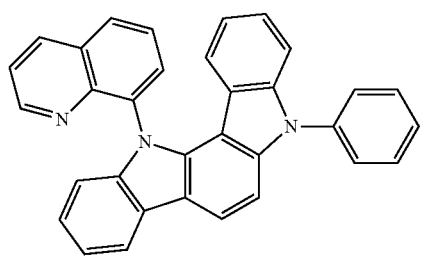
(29)
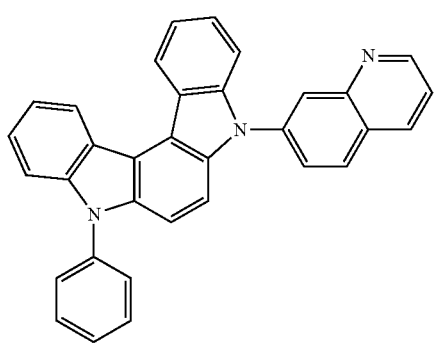
(33)
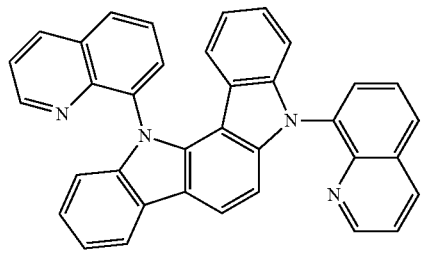
(30)
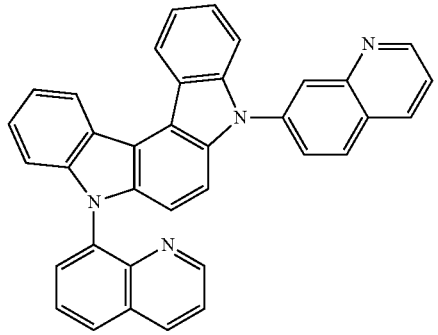
(34)
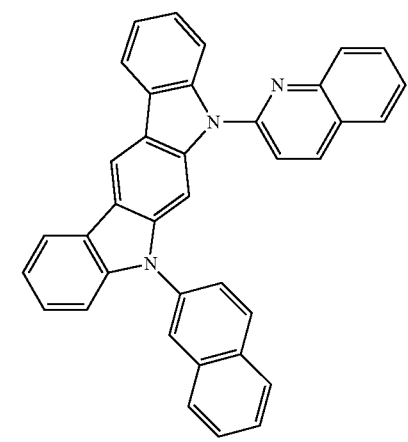
(31)
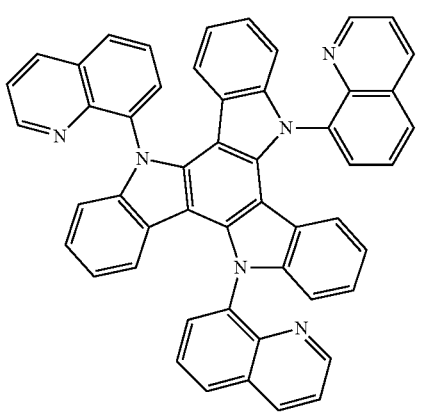
(35)

(36)

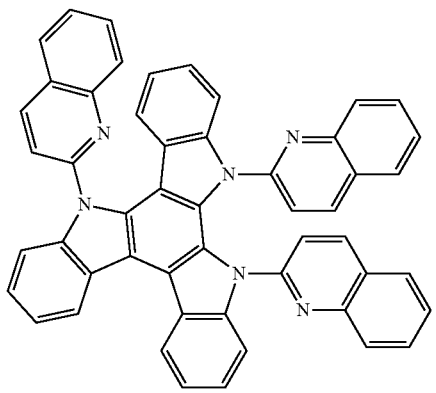

(37)

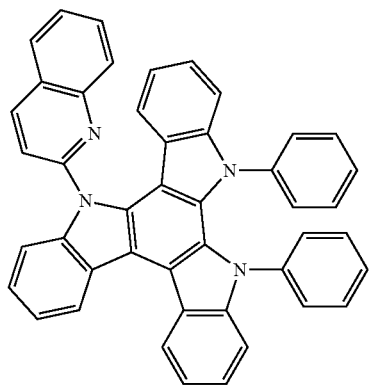

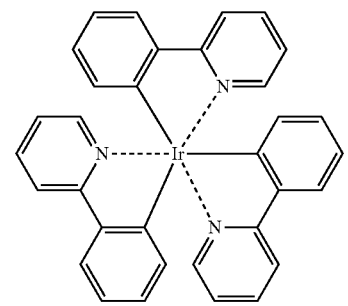

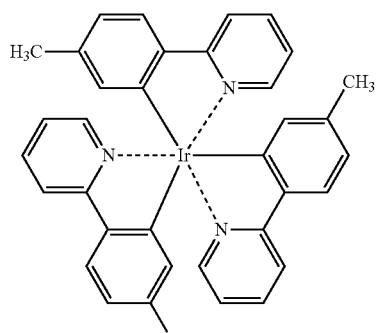

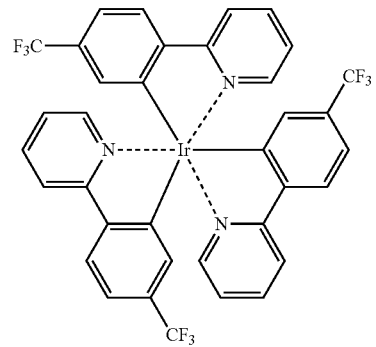

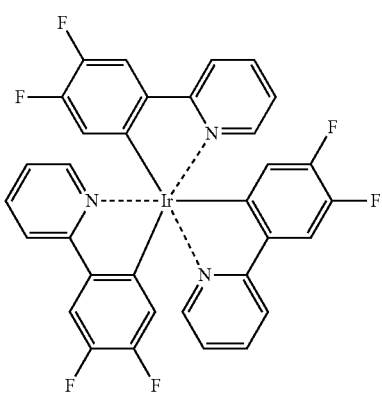

The compound for organic electroluminescent device of this invention provides an excellent organic electroluminescent device when it is incorporated in the organic layer of the device. Advantageously, the compound is incorporated in at least one organic layer selected from a light-emitting layer, a hole-transporting layer, an electron-transporting layer, and a hole-blocking layer. More advantageously, the compound is incorporated as a host material in the light-emitting layer comprising a phosphorescent dopant.

The materials for phosphorescent dopants to be used in the light-emitting layer are preferably organic metal complexes containing at least one metal selected from ruthenium, rhodium, palladium, silver, rhenium, osmium, iridium, platinum, and gold. Such organic metal complexes are well known in the aforementioned patent documents and elsewhere and a suitable complex can be selected from them and used in this invention.

Preferable phosphorescent dopants include complexes containing a noble metal element such as Ir in the center, typically Ir(ppy)3, complexes such as Ir(bt)2.acac3, and complexes such as PtOEt3. Examples of these complexes are shown below, but are not limited thereto.

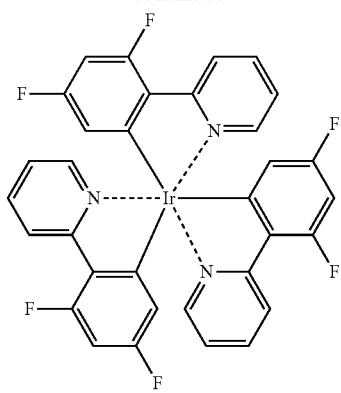
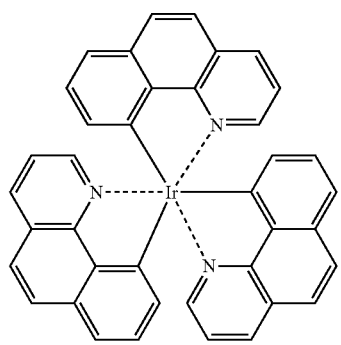
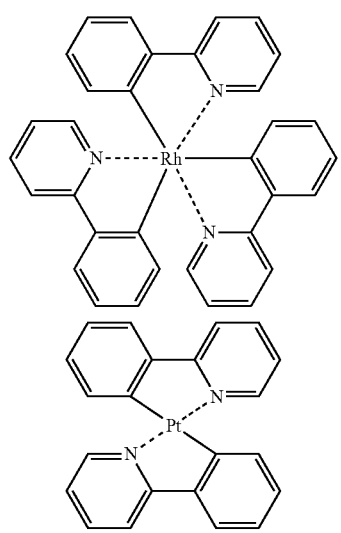
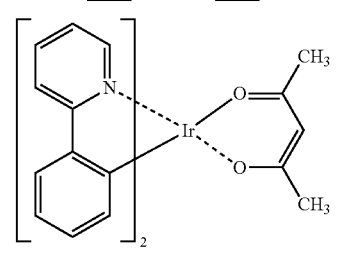
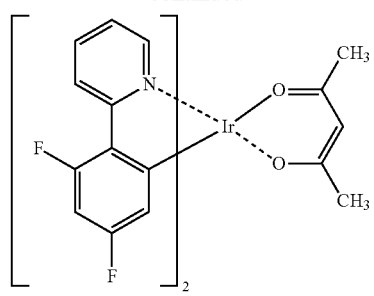
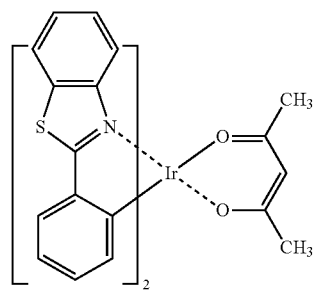
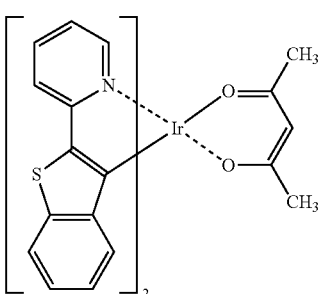
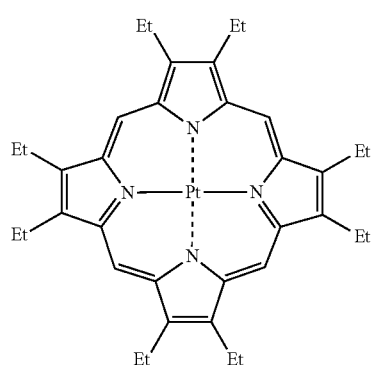
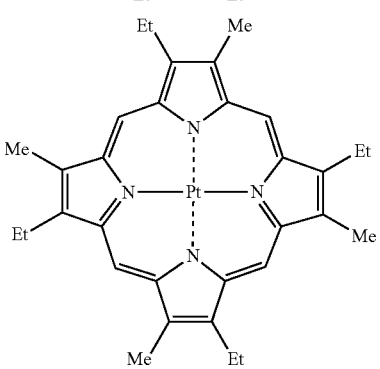

-continued

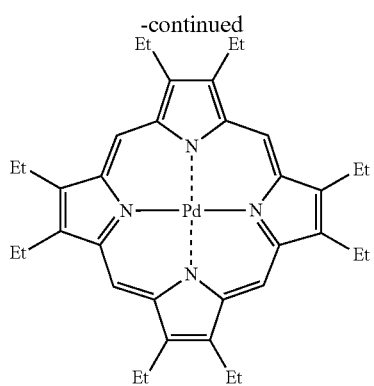

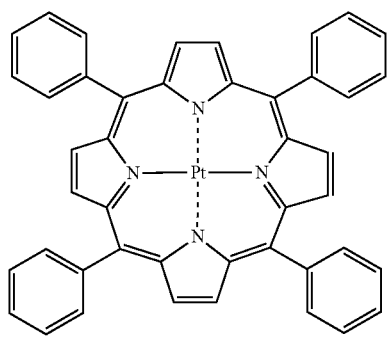

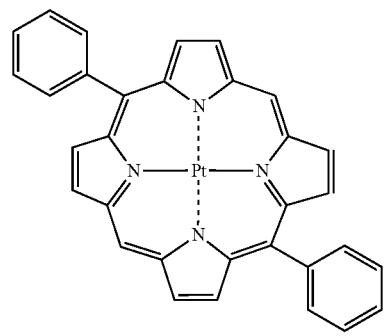

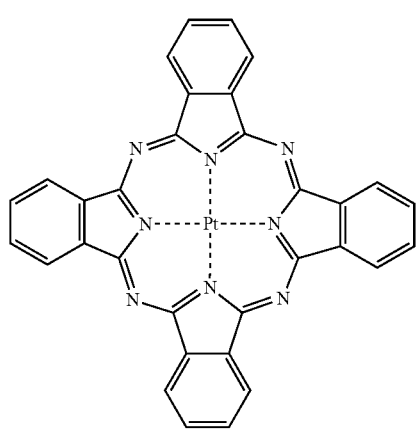

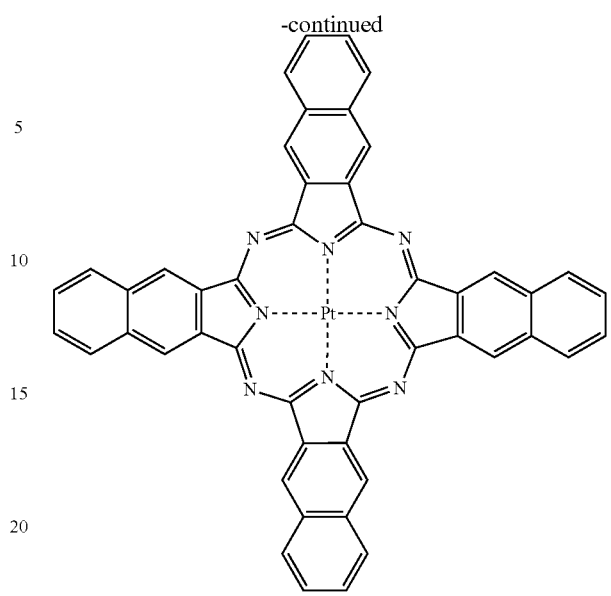

The content of the aforementioned phosphorescent dopant in the light-emitting layer is in the range of 2-20 wt %, preferably in the range of 5-10 wt %. In this case, the compound for organic EL device of this invention is preferably used as a host material and it is incorporated in the light-emitting layer while controlling its content at 50 wt % or more, preferably in the range of 80-95 wt %.

The structure of the organic EL device of this invention will be explained next with reference to the drawing, but it is not limited to the one illustrated in the drawing.

FIG. 1 schematically shows an example of the structure of an organic EL device generally used in this invention and the symbols in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention comprises a substrate, an anode, a light-emitting layer, and a cathode as essential layers; in addition, the device preferably contains a hole-injecting/transporting layer and an electron-injecting/transporting layer and, further, a hole-blocking layer disposed between the light-emitting layer and the electron-injecting/transporting layer. The term hole-injecting/transporting layer means a hole-injecting layer and/or a hole-transporting layer while the term electron-injecting/transporting layer means an electron-injecting layer and/or an electron-transporting layer.

The substrate 1 serves as a support for an organic EL device and the materials useful therefor include a quartz plate, a glass plate, a metal sheet, a metal foil, a plastic film, and a plastic sheet. In particular, a glass plate is preferred.

The anode 2 plays a role of injecting holes into the hole-injecting layer 3. The anode 2 is usually constituted of a metal such as aluminum, gold, silver, nickel, palladium, and platinum, a metal oxide such as an oxide of indium and/or tin (ITO), a metal halide such as copper iodide, carbon black, or an electrically conductive polymer such as poly(3-methylthiophene), polypyrrole, and polyaniline.

The light-emitting layer 5 is constituted of a light-emitting substance that emits light when excited by recombination of holes injected from the anode 2 and migrating through the hole-transporting layer 4 and electrons injected from the cathode 7 and migrating through the electron-transporting layer 6 upon application of an electrical field to the electrodes. The light-emitting layer 5 preferably comprises a dopant material and a host material consisting of the aforementioned compound for organic EL device as a light-emitting substance.

The cathode 7 plays a role of injecting electrons through the electron-transporting layer 6 into the light-emitting layer 5. The materials useful for the cathode 7 are preferably metals of low work function for efficient injection of electrons and examples include metals such as tin, magnesium, indium, calcium, cesium, aluminum, and silver and alloys thereof. Examples of the alloys include magnesium-silver alloys, magnesium-indium alloys, and aluminum-lithium alloys.

The hole-injecting layer 3, the hole-transporting layer 4, and the electron-transporting layer 6 are optional organic layers; the hole-injecting layer 3 is used for the purpose of enhancing the efficiency of injecting holes from the anode 2 into the hole-transporting layer 4 while the hole-transporting layer 4 and the electron-transporting layer 6 respectively transport holes and electrons to the light-emitting layer 5. An electron-injecting layer may be disposed between the cathode 7 and the electron-transporting layer 6. The materials useful for these layers are well known.

The materials for the hole-injecting layer include phthalocyanine compounds such as copper phthalocyanine (CuPC), organic compounds such as polyaniline and polythiophene, and oxides of metals such as vanadium, ruthenium, and molybdenum.

The materials for the hole-transporting layer include triazole derivatives, oxadiazole derivatives, imidazole derivatives, polyarylalkane derivatives, pyrazoline derivatives, pyrazolone derivatives, phenylenediamine derivatives, arylamine derivatives such as NPB, amino-substituted chalcone derivatives, oxazole derivatives, styrylanthracene derivatives, fluorenone derivatives, hydrazone derivatives, stilbene derivatives, silazan derivatives, aniline-based copolymers, and electrically conductive oligomers, especially thiophene oligomers.

The materials for the electron-transporting layer include metal complexes such as Alq3, 10-hydroxybenzo[h]quinoline metal complexes, oxadiazole derivatives, distyrylbiphenyl derivatives, silole derivatives, 3- or 5-hydroxyflavone metal complexes, benzoxazole metal complexes, benzothiazole metal complexes, trisbenzimidazolybenzene, quinoxaline compounds, phenanthroline derivatives, 2-t-butyl-9,10-N,N'-dicyanoanthraquinonediimine, n-type hydrogenated amorphous silicon carbide, n-type zinc sulfide, and n-type zinc selenide.

It is possible to build a structure that is the reverse of the structure shown in FIG. 1 by piling the cathode 7, the electron-transporting layer 6, the light-emitting layer 5, the hole-transporting layer 4, and the anode 2 one upon another in this order on the substrate 1. As described earlier, it is also possible to dispose the organic EL device of this invention between two substrates at least one of which is highly transparent. In this case of the reverse structure, it is also possible to add or omit a layer or layers as needed.

The organic EL device of this invention is applicable to a single device, a device with its structure arranged in array, or a device in which the anode and the cathode are arranged in X-Y matrix. This invention provides an organic EL device that is enhanced in the luminous efficiency and markedly improved in the driving stability compared with the conventional devices utilizing emission of light from the excited singlet state by incorporating a compound of a specified skeleton and a phosphorescent dopant in the light-emitting layer and the device can perform excellently in applications to full-color or multicolor panels.

EXAMPLES

This invention will be explained in more detail below with reference to the examples; however, this invention is not be limited to these examples and it can be reduced into practice in a variety of modes unless such a mode of practice exceeds the substance of this invention. The compound numbers in the examples correspond to the numbers assigned to the chemical formulas earlier cited in the specification.

Example 1

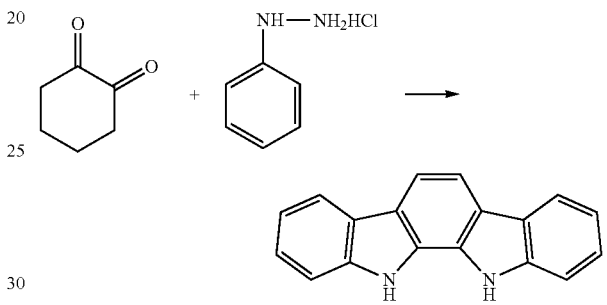

In a nitrogen-blanketed 2,000-ml three-necked flask were placed 33.3 g (297.0 millimoles) of 1,2-cyclohexanedione and 86.0 g (594.7 millimoles) of phenylhydrazine hydrochloride, then 1,000 ml of ethanol was added, and the mixture was stirred. Thereafter, 3.0 g (30.6 millimoles) of concentrated sulfuric acid was added dropwise to the flask over 5 minutes and the resulting mixture was heated to 65° C. and stirred for 4 hours. The mixture was then cooled to room temperature, the purplish brown crystals formed were collected by filtration, and the crystals were reslurried twice in 500 ml of ethanol and then dried under reduced pressure to yield 80.0 g (280.5 millimoles, 96.3% yield) of a purplish brown powder.

Then, 72.0 g (261.5 millimoles) of the aforementioned purplish brown powder was placed in a 1,000-ml three-necked flask, then 720 g of acetic acid and 72.0 g of trifluoroacetic acid were added, and the mixture was stirred. The mixture was then heated to 100° C. and stirred for 15 hours. The mixture was cooled to room temperature, the yellow crystals formed were collected by filtration, and the crystals were rinsed with 200 ml of acetic acid, then rinsed with 200 ml of hexane, and dried under reduced pressure to yield 30.0 g (117.1 millimoles, 44.8% yield) of white powder A'. White powder A' thus obtained is indolo[2,3-a]carbazole.

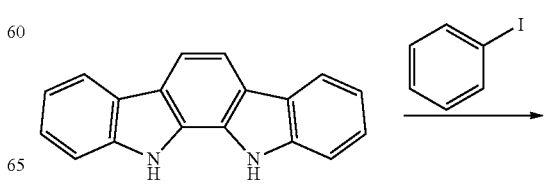

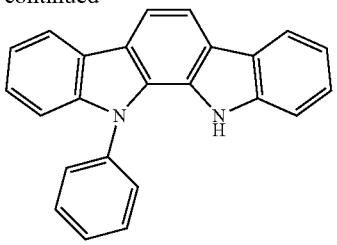

Next, 26.0 g (101.4 millimoles) of the white powder obtained above, 122.7 g (601.4 millimoles) of iodobenzene, 54.7 g (287.2 millimoles) of copper iodide, 66.7 g (482.6 millimoles) of potassium carbonate, and 800 ml of quinoline were placed in a nitrogen-blanketed 1,000-ml three-necked flask and the mixture was stirred. Then, the mixture was heated to 190° C. and stirred for 72 hours. The mixture was cooled to room temperature, 500 ml of water and 500 ml of dichloromethane were added, the mixture was stirred, and the yellow crystals formed were collected by filtration. The filtrate was transferred to a 2,000-ml separatory funnel and separated into an organic layer and an aqueous layer. The organic layer was washed three times with 500 ml of water, dehydrated over magnesium sulfate, the magnesium sulfate was filtered off, and the solvent was distilled off under reduced pressure. The residue was purified by column chromatography to yield 13.7 g (41.2 millimoles, 40.6% yield) of white solid A. White solid A thus obtained is 11-phenylindolo[2,3-a]carbazole.

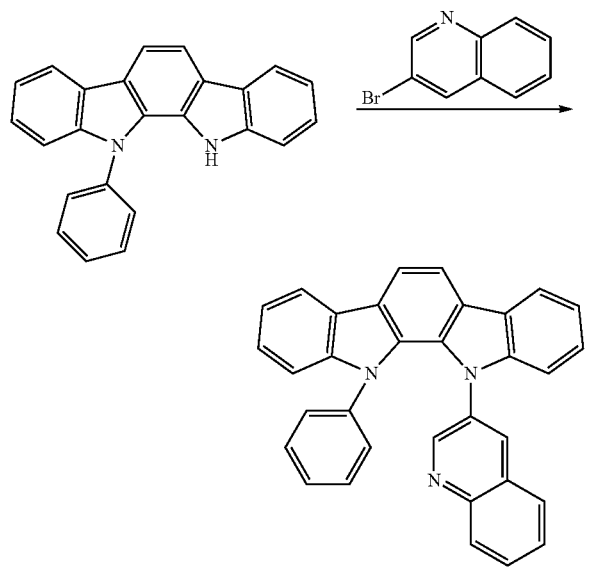

In a nitrogen-blanketed 100 ml three-necked flask were placed 0.52 g (2.33 millimoles) of palladium(II) acetate, 1.97 g (9.74 millimoles) of tri-tert-butylphosphine, and 45 ml of dehydrated xylene and the mixture was stirred. The mixture was then heated to 80° C. and stirred for 30 minutes to prepare the catalyst. Next, 15.4 g (46.3 millimoles) of 11-phenylindolo[2,3-a]carbazole, 14.5 g (69.7 millimoles) of 3-bromoquinoline, 18.8 g (195 millimoles) of sodium tert-butoxide, and 430 ml of dehydrated xylene were placed in a nitrogen-blanketed 1,000-ml three-necked flask and the mixture was stirred. The mixture was heated to 80° C., the catalyst solution prepared above was added, and the resulting mixture was heated to 130° C. and stirred for 17 hours. The mixture was cooled to room temperature, 340 ml of water added and stirred, and the yellow crystals formed were collected by filtration. The crystals were reslurried twice in 200 ml of methanol, purified by column chromatography, and then reslurried in toluene by application of heat to yield 12.0 g (26.1 millimoles, 56.4% yield) of yellow crystals. This yellow crystalline product is Compound 3. APCI-MS, m/z 460 [M+H]$^+$.

Example 2

An organic EL device constituted as in FIG. 1 with addition of an electron-injecting layer was fabricated. Applying the vacuum deposition process at a degree of vacuum of $4.0 \times 10^{-4}$ Pa, the constituent layers were deposited in thin film one upon another on a glass substrate on which a 150 nm-thick ITO anode had been formed. First, copper phthalocyanine (CuPC) was deposited on the ITO anode to a thickness of 20 nm as a hole-injecting layer. Then, NPB was deposited to a thickness of 40 nm as a hole-transporting layer. Next, Compound 3 as a host material and Ir(ppy)3 as a dopant were co-deposited from different evaporation sources on the hole-transporting layer to a thickness of 35 nm to form a light-emitting layer. At this point, the concentration of Ir(ppy)3 was 7.0 wt %. After this, Alq3 was deposited to a thickness of 40 nm as an electron-transporting layer. Further, lithium fluoride (LiF) was deposited on the electron-transporting layer to a thickness of 0.5 nm as an electron-injecting layer. Finally, aluminum (Al) as an electrode was deposited on the electron-injecting layer to a thickness of 170 nm to complete the fabrication of the organic EL device.

The organic EL device thus fabricated was connected to an outside power source and, when direct current voltage was applied, the device was confirmed to emit light with the characteristics shown in Table 1. In Table 1, the luminance, voltage, and luminous efficiency were measured at 10 mA/cm$^2$. The maximum wavelength of the spectrum of light emitted from the device was 517 nm and this proves that light is emitted from Ir(ppy)3.

Example 3

An organic EL device was fabricated as in Example 2 with the exception of using Compound 2 as a host material in the light-emitting layer.

Example 4

An organic EL device was fabricated as in Example 2 with the exception of using Compound 9 as a host material in the light-emitting layer.

Example 5

An organic EL device was fabricated as in Example 2 with the exception of using Compound 18 as a host material in the light-emitting layer.

Example 6

An organic EL device was fabricated as in Example 2 with the exception of using Compound 20 as a host material in the light-emitting layer.

Example 7

An organic EL device was fabricated as in Example 2 with the exception of using Compound 23 as a host material in the light-emitting layer.

Example 8

An organic EL device was fabricated as in Example 2 with the exception of using Compound 26 as a host material in the light-emitting layer.

Example 9

An organic EL device was fabricated as in Example 2 with the exception of using Compound 29 as a host material in the light-emitting layer.

Example 10

An organic EL device was fabricated as in Example 2 with the exception of using Compound 31 as a host material in the light-emitting layer.

Example 11

An organic EL device was fabricated as in Example 2 with the exception of using Compound 33 as a host material in the light-emitting layer.

Example 12

An organic EL device was fabricated as in Example 2 with the exception of using Compound 35 as a host material in the light-emitting layer.

Comparative Example 1

An organic EL device was fabricated as in Example 2 with the exception of using HMTPD in the hole-transporting layer and TAZ as a host material in the light-emitting layer.

Comparative Example 2

An organic EL device was fabricated as in Example 2 with the exception of using TAZ as a host material in the light-emitting layer.

The luminous characteristics were evaluated and the results are shown in Table 1. In Table 1, the luminance, voltage, and luminous efficiency were measured at 10 mA/cm$^2$. In each of Examples 2 to 12 and Comparative Examples 1 and 2, the maximum wavelength of the spectrum of light emitted from the device was 517 nm and this proves that light is emitted from Ir(ppy)3.

TABLE 1

|  | Compound No | Luminance (cd/m$^2$) | Voltage (V) | Luminous efficiency (1 m/W) |
|---|---|---|---|---|
| Example 2 | 3 | 2620 | 5.2 | 15.8 |
| 3 | 2 | 2760 | 6.2 | 14.0 |
| 4 | 9 | 3150 | 6.5 | 15.2 |
| 5 | 18 | 2850 | 6.9 | 13.0 |
| 6 | 20 | 2945 | 5.1 | 18.1 |
| 7 | 23 | 2860 | 5.2 | 17.3 |
| 8 | 26 | 2560 | 5.5 | 14.6 |
| 9 | 29 | 3020 | 5.2 | 18.2 |

TABLE 1-continued

|  | Compound No | Luminance (cd/m$^2$) | Voltage (V) | Luminous efficiency (1 m/W) |
|---|---|---|---|---|
| 10 | 31 | 2975 | 5.4 | 17.3 |
| 11 | 33 | 3040 | 5.6 | 17.1 |
| 12 | 35 | 2080 | 6.7 | 9.8 |
| Comparative example 1 | — | 2050 | 13.2 | 4.9 |
| 2 | — | 1270 | 9.5 | 4.2 |

INDUSTRIAL APPLICABILITY

The organic EL device of this invention is capable of emitting light of high luminance at high efficiency with application of low voltage. Hence, the device is of high technical value because of its potential applicability to flat panel displays (for example, in office computers and wall-hanging television sets), vehicle-mounted display devices, mobile phone displays, light sources utilizing the characteristics of planar light emitters (for example, light sources for copiers and backlight sources of liquid crystal displays and instruments), signboards, and beacon lights.

The invention claimed is:

1. A compound for an organic electroluminescent device represented by the following general formula (1):

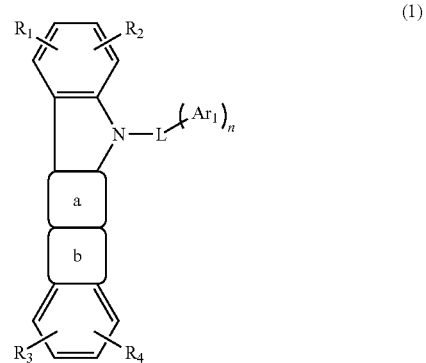

(1)

(a1)

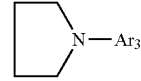

(b1)

wherein ring a is an aromatic or heterocyclic ring fused to two adjacent rings and represented by formula (a1), and ring b is a heterocyclic ring fused to two adjacent rings and represented by formula (b1);

X is CR or N;

L is an aromatic heterocyclic group of a fused-ring structure with a valence of (n+1);

Ar$_1$ and Ar$_3$ each is independently an alkyl group, an aralkyl group, or a C$_6$-C$_{15}$ substituted or unsubstituted aromatic hydrocarbon or C$_3$-C$_{15}$ substituted or unsubstituted aromatic heterocyclic group and Ar$_3$ is never a nitrogen-containing six-membered ring;

R and R$_1$ to R$_5$ each is independently hydrogen, an alkyl group, an aralkyl group, an alkenyl group, an alkynyl group, a cyano group, a nitro group, an alkoxyl group, an alkylsulfonyl group, a haloalkyl group, a hydroxyl group, or a substituted or unsubstituted aromatic hydrocarbon group; and n is an integer of 0-5.

2. The compound for an organic electroluminescent device as described in claim 1, wherein the compound is represented by the following general formula (2):

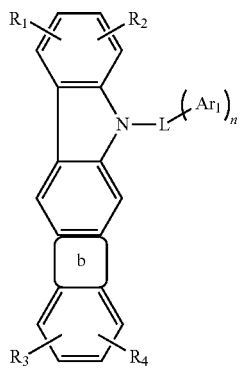

(2)

wherein ring b, L, $Ar_1$, $R_1$ to $R_4$, and n of formula (2) have the same meanings as ring b, L, $Ar_1$, $R_1$ to $R_4$, and n, respectively, of general formula (1).

3. The compound for an organic electroluminescent device as described in claim 1, wherein the compound is represented by the following general formula (3):

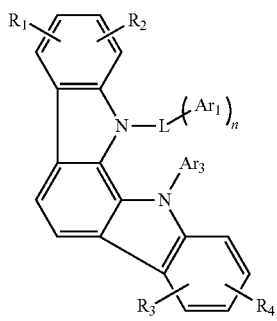

(3)

wherein L, $Ar_1$, $Ar_3$, $R_1$ to $R_4$, and n of formula (3) have the same meanings as L, $Ar_1$, $Ar_3$, $R_1$ to $R_4$, and n, respectively, of general formula (1).

4. The compound for an organic electroluminescent device as described in claim 1, wherein, in general formula (1), L is an aromatic heterocyclic group of a fused-ring structure containing 6 to 20 carbon atoms with a valence of (n+1).

5. An organic electroluminescent device comprising an organic layer comprising the compound for an organic electroluminescent device described in any one of claims 1 to 3.

6. The organic electroluminescent device as described in claim 5, wherein the organic layer comprising a compound for an organic electroluminescent device is at least one layer selected from the group consisting of a light-emitting layer, a hole-transporting layer, a hole-injecting layer, an electron-transporting layer, an electron-injecting layer, and a hole-blocking layer.

7. The organic electroluminescent device as described in claim 5, wherein the organic layer comprising a compound for organic electroluminescent device is a light-emitting layer and the said light-emitting layer comprises a phosphorescent dopant and the said compound for organic electroluminescent device as a host material.

8. The compound for an organic electroluminescent device as described in claim 1, wherein the compound has only one indolocarbazole group.

9. The compound for an organic electroluminescent device as described in claim 1, wherein L is an unsubstituted aromatic heterocyclic group of a fused-ring structure composed of 2-3 rings with a valence of (n+1).

10. The compound for an organic electroluminescent device as described in claim 1, wherein L is the aromatic heterocyclic group selected from the group consisting of benzothiophene, benzothiazole, thianthrene, isobenzofuran, benzoxazole, chromene, xanthene, phenoxathiin, indolizine, isoindole, indole, benzimidazole, indazole, benzotriazole, purine, quinolizine, isoquinoline, quinoline, phthalazine, naphthyridine, quinoxaline, quinazoline, cinnoline, pterizine, carbazole, carboline, phenanthridine, acridine, perimidine, phenanthroline, phenazine, phenothiazine, phenoxazine, and dibenzodioxin.

* * * * *